United States Patent [19]

Bither, Jr. et al.

[11] 4,322,358

[45] Mar. 30, 1982

[54] PREPARATION OF FURAN

[75] Inventors: Tom A. Bither, Jr., Wilmington, Del.; William R. McClellan, Kennett Square, Pa.

[73] Assignee: E. I. Du Pont de Nemours and Company, Wilmington, Del.

[21] Appl. No.: 85,494

[22] Filed: Oct. 17, 1979

[51] Int. Cl.$^3$ .......................................... C07D 307/36
[52] U.S. Cl. ............................... 260/346.11; 252/437; 252/439; 252/462; 252/464; 252/467; 252/468; 252/470
[58] Field of Search ..................................... 260/346.11

[56] References Cited

U.S. PATENT DOCUMENTS

| | | | |
|---|---|---|---|
| 2,900,396 | 8/1959 | Harrison | 260/346.11 |
| 3,238,225 | 3/1966 | Brill et al. | 260/346.11 |
| 3,328,315 | 6/1967 | Callahan et al. | 252/432 |
| 3,716,545 | 2/1973 | Ripley | 260/346.11 X |
| 3,894,055 | 7/1975 | Farha et al. | 260/346.11 |
| 3,894,056 | 7/1975 | Bertus et al. | 260/346.11 |
| 3,906,009 | 9/1975 | Farha | 260/346.11 |
| 3,912,763 | 10/1975 | Farha et al. | 260/346.11 |
| 3,928,389 | 12/1975 | Farha et al. | 260/346.11 |
| 4,026,820 | 5/1977 | Farha et al. | 252/432 |
| 4,039,476 | 8/1977 | Bertus et al. | 252/437 |

Primary Examiner—Richard Raymond

[57] ABSTRACT

Catalytic vapor phase process wherein the feed stream comprising, on a molar basis, the sum of which is 100%, 10-32% of at least one linear unsaturated $C_4$-hydrocarbon selected from 1-butene, 2-butene and 1,3-butadiene, 10-25% oxygen, 3-30% water and 13-77% inert diluent, is contacted with a modified bismuth molybdenum oxide catalyst at 350°-600° C. at a pressure of at least 1 atmosphere (about 100 kPa) for 0.1-10 seconds, said catalyst being selected from:

(a) $BiMo_aM_bQ_cR_dO_x$ wherein M is at least one element selected from In, Ce, Cr, Fe and Cu, Q is at least one element selected from V, P, Sb and Te, R is Na or Ag, a is 0.7-60.0, b is 0.1-33.0, c is 0-7.0, d is 0-1.5 and x is such a number as is necessary to satisfy the valences of the elements, with the proviso that $a/1+b \geq 0.5$ and $a/1+b+c \geq 0.19$ and the proviso that $c>0$ when $d>0$; and (b) $BiMo_aAs_bZ_cO_x$ wherein Z is at least one element selected from Na and Ca, a is 1.3-2.0, b is 0.1-0.3, c is 0.3-0.7 and x is such a number as is necessary to satisfy the valences of the elements, to produce an off-gas containing at least 1% furan.

12 Claims, No Drawings

PREPARATION OF FURAN

DESCRIPTION

TECHNICAL FIELD

This invention relates to a vapor phase catalytic process for producing furan from a linear monoolefin or diolefin having four carbon atoms.

BACKGROUND ART

Processes for the vapor phase oxidation of diolefins to furan utilizing selected catalysts such as heterogeneous bismuth molybdates, manganese molybdates and tungstates and processes for the oxidative dehydrogenation of alkenes or alkadienes to furan with selected transition metal phosphate catalysts are well known in the art. Although such processes use low to high concentrations of hydrocarbon in the gaseous feed mixtures, generally, the hydrocarbon feed level is no greater than 5%, in which case the concentration of furan in the resultant off-gases is less than 1%. Because of the low concentrations of furan realized by such processes, isolation of the furan may be excessively costly and/or difficult due to process inefficiencies, such as inordinately high compressor demands, vapor entrainment and the like.

Since the furan concentration index, a measure of the effectiveness of the process in producing furan, is the product of the concentration of $C_4$-hydrocarbon in the feed mixture $\times$ $C_4$-hydrocarbon conversion $\times$ furan selectivity, it is imperative that these three variables be maximized for high furan production. The term "$C_4$-hydrocarbon conversion" is defined, in %, as 100 times the number of moles of $C_4$-hydrocarbon converted to oxidation products other than butadiene divided by the number of moles of $C_4$-hydrocarbon in the initial feed mixture. The term "selectivity" is defined, in %, as 100 times the number of moles of a specific oxidation product produced in the reaction and normalized to a $C_4$-base divided by the total number of moles of $C_4$-hydrocarbon converted to oxidation products other than butadiene.

One method of obtaining a higher ultimate furan concentration is to increase the hydrocarbon feed concentration without incurring simultaneous decreases in hydrocarbon conversion and/or furan selectivity. In general, such an approach, using known bismuth molybdate catalysts and high concentrations of the unsaturated hydrocarbon, at conversion levels of 12% or greater, even in the presence of excess oxygen in the gas exit stream, results in marked decreases in furan selectivity and sharp increases in the production of carbon oxides and, ultimately, cracking products due to severe coking of the catalysts.

The primary object of this invention, therefore, is to provide a catalytic process for the vapor phase oxidation of a diolefin to furan, which process uses high concentrations (at least 10%) of the hydrocarbon in the feed stream, without significant losses in hydrocarbon conversion or furan selectivity, and yields a furan concentration in the off-gases of at least 1%.

All percentages disclosed herein, unless otherwise specified, are mole percentages.

DISCLOSURE OF INVENTION

For further comprehension of the invention, and of the objects and advantages thereof, reference may be made to the following description and to the appended claims in which the various novel features of the invention are more particularly set forth.

The invention resides in a process wherein a linear unsaturated $C_4$-hydrocarbon (1-butene, 2-butene, 1,3-butadiene, or a mixture thereof) is reacted with oxygen, under carefully controlled concentrations and reaction conditions, over a selective, supported or unsupported, modified bismuth molybdate catalyst. The active and selective catalysts of the process of the invention are capable of producing furan at an off-gas concentration of greater than 1%, preferably at least 1.8%, without inducing cracking or coking, using a feed mixture containing 10-32% $C_4$-hydrocarbon and 10-25% oxygen. Since 1,3-butadiene is the $C_4$-hydrocarbon which is directly oxidized to furan in the reaction, when the cheaper 1- and/or 2-butenes are employed as the feedstock, they undergo oxidative dehydrogenation to 1,3-butadiene in the initial step of the reaction. The bismuth molybdate species present in the catalyst of the process of this invention are capable of rapidly converting these linear $C_4$-alkenes into 1,3-butadiene prior to its oxidation to furan.

More specifically, the invention resides in the catalytic vapor phase process wherein the feed stream comprising, on a molar basis, the sum of which is 100%, 10-32% of at least one linear unsaturated $C_4$-hydrocarbon selected from 1-butene, 2-butene and 1,3-butadiene, 10-25% oxygen, 3-30% water and 13-77% inert diluent, is contacted with a modified bismuth molybdenum oxide catalyst at 350°-600° C. at a pressure of at least 1 atmosphere (about 100 kPa) for 0.1-10 seconds, said catalyst being selected from:

(a) $BiMo_aM_bQ_cR_dO_x$ wherein M is at least one element selected from In, Ce, Cr, Fe and Cu, Q is at least one element selected from V, P, Sb and Te, R is Na or Ag, a is 0.7-60.0, b is 0.1-39.8, c is 0-7.0, d is 0-1.5 and x is such a number as is necessary to satisfy the valences of the elements, with the proviso that $a/1+b \geq 0.5$ and $a/1+b+c \geq 0.19$ and the proviso that $c>0$ when $d>0$; and (b) $BiMo_aAs_bZ_cO_x$ wherein Z is at least one element selected from Na and Ca, a is 1.3-2.0, b is 0.1-0.3, c is 0.3-0.7 and x is such a number as is necessary to satisfy the valences of the elements, to produce an off-gas containing at least 1% furan. In preferred embodiments of the process, the feed stream comprises 25-29% $C_4$-hydrocarbon, 14-20% oxygen, 13-20% water and 31-48% inert diluent, the temperature is 450°-550° C., the pressure is 1-3 atmospheres (about 100-300 kPa) and the catalyst is selected from $BiMo_3InO_x$, $BiMo_{1.5}In_{0.5}P_{0.5}O_x$, $BiMo_{1.56}In_{0.11}P_{0.11}Ag_{0.11}O_x$, $BiMo_{6.67}Ce_{0.67}O_x$, $BiMo_{2.67}In_{0.44}Cr_{0.44}P_{0.11}O_x$ and $BiMo_{1.7}As_{0.3}Ca_{0.65}O_x$. It is to be understood that the formulas for these catalysts are written empirically so that one gram atom of bismuth is shown in each formula. Equivalent formulas can be written, wherein more or less than one gram atom of bismuth is shown, and wherein the order of recitation of the elements is varied. For example, $BiMo_{1.7}As_{0.3}Ca_{0.65}O_x$ can be written, as in Example 26, as $Ca_{3.25}Bi_5As_{1.5}Mo_{8.5}O_x$.

The catalysts for this oxidation process comprise mixed modified bismuth molybdenum oxides of Mo/Bi atom ratio of 0.67-60/1 plus modifying oxides of In, Ce, Cr, Fe, Cu, V, P, As, Sb, Te, Na, Ag and/or Ca in varying amounts depending upon the selection of modifiers introduced into the mixed bismuth molybdenum oxides.

The catalyst used in the process of the invention can be prepared in either unsupported or supported form and, if supported, they can be prepared in a range of particle sizes for use either in fixed- or fluid bed type operations. Unsupported catalysts can be prepared by combining the appropriate metal salts and/or oxides in water, followed by evaporating to dryness with stirring and subsequently firing at the desired temperature, or they can be prepared from the appropriate oxides, carbonates and the like by use of standard solid state reaction techniques.

If supported catalysts are desired, preformed supports such as silica, alumina, mixed silica-aluminas and silicon carbide can be impregnated with aqueous solutions and/or slurries of the desired compositions, followed by evaporation to dryness and subsequent calcination at the desired temperature. Silica at a concentration of about 50 weight % is a preferred support for the catalysts described herein, and the preferred method of incorporating this support into the catalysts is to mix a colloidal silica solution with aqueous solutions and/or slurries of the desired compositions, followed by either gelling these mixtures or concentrating them to low volume with stirring, using gentle heat ($\sim 100°$ C.), removing the residual water at a temperature of about 100° C., and then calcining for the desired time and temperature. If a fluid bed type catalyst is desired, the colloidal silica solution containing the requisite catalyst components and at the appropriate viscosity can be spray dried prior to the calcining step.

If the catalyst compositions described herein lose activity during use through partial reduction or through carbonization, they can be regenerated by refiring in air at substantially the same temperature as that used in the initial calcination step. Calcination temperatures for these catalysts can vary from about 350° to 800° C. with the preferred temperature range being 500°–600° C. Calcination times can vary from 3 to 36 hours with the preferred time being about 6–18 hours.

To be an economically viable process, the concentration of furan in the off-gases must be at least 1%. Assuming optimum catalyst performance, 25% $C_4$-conversion and 40% furan selectivity, a minimum $C_4$-hydrocarbon concentration of about 10% in the feed stream is necessary in order to obtain the 1% concentration of furan in the off-gases, that is, $100(0.1 \times 0.25 \times 0.4) = 1.0\%$. Depending upon the specific catalyst and feed mixture, an upper limit of 28–30% $C_4$-hydrocarbon feed concentration can be employed without inducing cracking. A hydrocarbon concentration higher than 32% should not be used. The optimum hydrocarbon concentration is 25–29%.

The oxygen used in the reaction of the process of the invention can be introduced in the form of pure oxygen or as a mixture with gaseous inert diluents such as nitrogen, carbon dioxide, argon, helium and/or water. Generally, the gaseous inert diluent is nitrogen. The amount of oxygen in the feed stream is 10–25%, with about 14–20% being preferred. When air is used to provide the oxygen, some bottled (tonnage) oxygen can be employed in conjunction with air to obtain the requisite concentrations. As already indicated hereinabove, the inert diluent comprises 13–77%, preferably 31–48%, of the feed stream.

The presence of some water in the feed has been found to have a beneficial effect on the furan selectivity. It is postulated that this species tends to suppress carbonaceous build-up on the catalyst through removal by way of the water-gas reaction. The amount of water in the feed stream is 3–30%, with 13–20% being preferred.

The vapor phase oxidation of 1-butene, 2-butene, and/or 1,3-butadiene admixed with oxygen, water and inert gases to furan is carried out in a heated reactor containing the appropriate catalyst having a particle size sufficient to avoid the build-up of excessive back pressure. For a fixed bed process, catalyst particle size can vary from about 4 to 60 mesh (U.S. Sieve Series), with 10–20 mesh being preferred.

Reaction temperatures can vary from about 350° to 600° C., with the preferred temperature range being about 450°–550° C., depending upon the catalyst activity. Reactor pressure can vary from atmospheric to superatmospheric, with 1–3 atmospheres (about 100–300 kPa) being preferred. Nominal contact times, that is, the time that the feed stream is in contact with the catalyst, as expressed by the ratio of bulk catalyst volume to gaseous feed volume passed over the catalyst per second (gas flows calculated at room temperature) can vary from about 0.1 to 10 seconds, with about 0.25–1 second being preferred.

Oxidation products normally produced in this reaction in addition to the desired furan comprise carbon dioxide, carbon monoxide, acrolein and lesser amounts of other species which can include, depending upon the specific catalyst employed, such compounds as ethylene, propylene, formaldehyde, maleic anhydride and/or monobasic acids such as acrylic acid. The amounts of feed gases employed and gaseous oxidation products produced in the reactions described herein were determined by means of standard gas chromatographic analysis. Acids produced were determined by titration of aqueous aliquots through which the reactor off-gases were bubbled.

The following examples serve to illustrate specific embodiments of the invention. In these examples are described detailed typical procedures which are used to prepare some of the preferred catalysts and the performance of these catalysts under operating conditions, at atmospheric pressure (about 100 kPa), wherein furan is produced by way of the vapor phase oxidation of linear unsaturated $C_4$-hydrocarbons. In the disclosure of each example, only the concentration of $C_4$-hydrocarbon is given; the concentrations of the other components of the feed stream are within the ranges disclosed hereinabove.

EXAMPLE 1

Silica Supported Catalyst—Gel Preparative Technique—1,3-Butadiene Feed

A. Preparation of Catalyst BiIn $Mo_3O_x/SiO_2$

To a stirred silica sol of 180 g of Ludox ® LS (30% concentration of $SiO_2$) was added in two simultaneous streams: (a) 35.59 g of $(NH_4)_6Mo_7O_{24}.4H_2O$ dissolved in 40 ml of $H_2O$ and (b) 7.72 g of In metal and 14.04 g of Bi metal dissolved in $HNO_3$ so as to have a final volume of about 70 ml. The resultant slurry was gelled by the addition of sufficient conc. $NH_4OH$ so as to bring the final pH of the system to a value of about 5.8. The gel was dried for about 16 hrs at 120° C. and then gently air fired to about 400° C. so as to drive off the residual $NH_4NO_3$ present from the neutralization reaction. The resultant solids were screened to 10–20 mesh and after air firing for about 16 hours at 550° C. were ready for catalyst use. The surface area was about 53 m²/g.

B. Oxidation of 1,3-Butadiene over $BiInMo_3O_x/SiO_2$

A feed containing 29.9% 1,3-butadiene was passed over 3 cc of 10–18 mesh $BiInMo_3O_x/SiO_2$ catalyst in a fixed-bed reactor at a flow rate of about 500 cc/min at reaction temperatures of 470°, 498°, and 506° C. Conversion and selectivity data plus percent furan in the off-gases obtained in the resultant oxidations are listed in Table I.

TABLE I

| Temp. (°C.) | $C_4$ Conv. (%) | Selectivity (%) | | | | | % Furan in Off-gases |
|---|---|---|---|---|---|---|---|
| | | Furan | Acrolein | $CO_2$ | CO | Other | |
| 470 | 11 | 34 | 12 | 35 | 16 | 3 | 1.1 |
| 498 | 19 | 28 | 12 | 33 | 22 | 5 | 1.6 |
| 506 | 19 | 32 | 11 | 36 | 17 | 4 | 1.8 |

C. Stability of $BiInMo_3O_x/SiO_2$ Catalyst with Use

The $BiInMo_3O_x/SiO_2$ catalyst was tested over a six-day period for the generation of furan from feeds containing some 26.3–28.4% 1,3-butadiene. After an initial decrease in activity, the production of furan was observed to level out during this test interval. Data are as follows in Table II.

TABLE II

| | Reaction Temperature (°C.) | | | | | |
|---|---|---|---|---|---|---|
| | ~500° | | | ~530° | | |
| Day of Test | $C_4$ Conv. | Furan Select. | % Furan in Off-gases | $C_4$ Conv. | Furan Select. | % Furan in Off-gases |
| 1 | 21 | 31 | 1.7 | 23 | 30 | 1.8 |
| 2 | 14 | 37 | 1.5 | 18 | 36 | 1.8 |
| 3 | — | — | — | 19 | 39 | 2.1 |
| 4 | 12 | 39 | 1.2 | 17 | 37 | 1.7 |
| 5 | 13 | 41 | 1.5 | 17 | 36 | 1.7 |
| 6 | — | — | — | 18 | 36 | 1.7 |

EXAMPLE 2

Silica Supported Catalyst—Gel Preparative Technique—1,3-Butadiene Feed

A. Preparation of Catalyst $AgInBi_9Mo_{14}PO_x/SiO_2$

To a stirred silica sol of 170 g of Ludox ® LS was added a solution of 1.52 g of $(NH_4)_2HPO_4$ in 5 ml of $H_2O$. Two simultaneous streams of liquid were subsequently added that comprised: (a) 28.41 g of $(NH_4)_6Mo_7O_{24}.4H_2O$ dissolved in 28 ml of $H_2O$ and (b) 1.32 g of In metal dissolved in $HNO_3$ and then added to a solution of 1.95 g of $AgNO_3$ and 50.17 g of $Bi(NO_3)_3.5H_2O$ in a mixture of 20 ml of $H_2O$ and 8 ml of $HNO_3$. The resultant slurry was gelled by the addition of sufficient conc. $NH_4OH$ so as to bring the final pH of the system to a value of about 6.8. The gel was dried for about 16 hrs at 120° C. and then gently air fired to decompose the residual $NH_4NO_3$ present from the neutralization reaction. The resultant solids were air fired for about 6 hrs at 600° C. and, following sieving to 10–20 mesh, were ready for catalyst use.

B. Oxidation of 1,3-Butadiene over $AgInBi_9Mo_{14}PO_x/SiO_2$

A feed containing 26.1% 1,3-butadiene was passed over 3 cc of 10–18 mesh $AgInBi_9Mo_{14}PO_x/SiO_2$ catalyst in a fixed-bed reactor at a flow rate of about 475 cc/min at reaction temperatures of about 500° and 530° C. Conversion and selectivity data plus percent furan in the off-gases obtained in the resultant oxidations are listed in Table III.

TABLE III

| Temp. (°C.) | $C_4$ Conv. (%) | Selectivity (%) | | | | | % Furan in Off-gases |
|---|---|---|---|---|---|---|---|
| | | Furan | Acrolein | $CO_2$ | CO | Other | |
| 501 | 15 | 37 | 16 | 27 | 16 | 4 | 1.4 |
| 530 | 21 | 36 | 14 | 28 | 18 | 4 | 2.0 |
| 499 | 13 | 38 | 15 | 28 | 15 | 4 | 1.3 |

EXAMPLE 3

Unsupported Catalyst—Aqueous Slurry/Dry Preparative Technique—1,3-Butadiene Feed A. Preparation of Catalyst $BiCe_{1.4}Mo_{16}O_x$ A solution of 14.55 g of $Bi(NO_3)_3.5H_2O$ and 18.50 g of $Ce(NO_3)_3.6H_2O$ in 36 ml of $H_2O$ and 3.6 ml of $HNO_3$ was added with stirring to a solution of 85.75 g of $(NH_4)_6Mo_7O_{24}.4H_2O$ in 400 ml of $H_2O$ that was heated on a steam bath. The resultant slurry was dried down on the steam bath; the residue was dried for about 16 hrs at 120° C. and, after a gentle heating at about 300° C. to decompose the nitrates present, was air fired for 6 hrs at 575° C. Following coarse crushing and screening to 10–20 mesh, the catalyst was ready for use. Its surface area was about 3.6 m²/g.

B. Oxidation of 1,3-Butadiene over $BiCe_{1.4}Mo_{16}O_x$

A feed containing about 29%, 1,3-butadiene was passed over 3 cc of 10–18 mesh $BiCe_{1.4}Mo_{16}O_x$ catalyst in a fixed bed reactor at a flow rate of about 500 cc/min at reaction temperatures of 475°, 510°, and 530° C. Conversion and selectivity data plus percent furan in the off-gases obtained in the resultant oxidations are listed in Table IV.

TABLE IV

| Temp. (°C.) | $C_4$ Conv. (%) | Selectivity (%) | | | | | % Furan in Off-gases |
|---|---|---|---|---|---|---|---|
| | | Furan | Acrolein | $CO_2$ | CO | Other | |
| 475 | 14 | 43 | 13 | 25 | 15 | 4 | 1.7 |
| 510 | 18 | 38 | 13 | 25 | 19 | 5 | 2.0 |
| 530 | 19 | 34 | 14 | 24 | 21 | 7 | 1.9 |

EXAMPLE 4

Unsupported Catalyst—Solid State Preparation 1,3-Butadiene Feed

A. Preparation of Catalyst $Ce_{8.53}Bi_{0.3}Fe_{0.1}TeMo_{12}O_x$

A mixture of 22.02 g of $CeO_2$, 25.91 g of $MoO_3$, 2.39 g of $TeO_2$, 1.45 g of $Bi_2O_3$, and 0.12 g of $Fe_2O_3$ was wet-ground to a fine paste under acetone and then air dried. The resultant powder was prefired in air for one hour at 500° C. and then reground and air dried as before. It was then air fired for 6 hrs at 550° C. The final product was reground again and then pelleted to 10–20 mesh size for catalyst use.

B. Oxidation of 1,3-Butadiene over $Ce_{8.53}Bi_{0.3}Fe_{0.1}TeMo_{12}O_x$

A feed containing about 28.7% 1,3-butadiene was passed over 3 cc of 10–18 mesh $Ce_{8.53}Bi_{0.3}Fe_{0.1}TeMo_{12}O_x$ catalyst in a fixed-bed reactor at a flow rate of about 500 cc/min. At a reaction temperature of 528° C., a butadiene conversion of about 14% resulted in the generation of furan at a selectivity of about 30%, giving a concentration of about 1.2% furan in the resultant off-gases.

EXAMPLE 5

Gel Preparation—1,3-Butadiene/1-butene Feed

A. Preparation of Catalyst $Na_{2.1}Bi_{6.3}AsMo_{9.25}O_x/SiO_2$

To a stirred silica sol of 90 g of Ludox® LS was added a solution of 1.6 g of $(NH_4)H_2AsO_4$ in 5 ml of $H_2O$ followed by a solution of 2.5 g of $Na_2MoO_4.2H_2O$ in 10 ml of $H_2O$. Two simultaneous streams of liquid were then added that comprised: (a) 30.6 g of $Bi(NO_3)_3.5H_2O$ dissolved in 16 ml of $H_2O$ and 1.6 ml of $HNO_3$ and (b) 14.03 g of $(NH_4)_6Mo_7O_{24}.4H_2O$ dissolved in 18 ml of $H_2O$. The resultant slurry was gelled by the addition of 20 ml of conc. $NH_4OH$; the gel was then dried at about 120° C. The resultant dried solids were calcined in air at 450° C. for about 18 hrs and then for about 5 hrs at 630° C. Following sieving, the catalyst was ready for use.

B. Oxidation of 1-Butene/1,3-Butadiene over $Na_{2.1}Bi_{6.3}AsMo_{9.25}O_x/SiO_2$ A feed containing about 3.8% 1-butene and 24.4% 1,3-butadiene was passed over 3 cc of 10–20 mesh $Na_{2.1}Bi_{6.3}AsMo_{9.25}O_x/SiO_2$ catalyst in a fixed-bed reactor at a flow rate of about 420 cc/min at temperatures of 555°, 563°, and 570° C. Conversion and selectivity data plus percent furan in the resultant off-gases are listed in Table V.

TABLE V

| Temp. (°C.) | $C_4$ Conv. (%) | Selectivity (%) | | | | | % Furan in Off-gases |
|---|---|---|---|---|---|---|---|
| | | Furan | Acrolein | $CO_2$ | CO | Other | |
| 555 | 11 | 42 | 12 | 27 | 18 | 1 | 1.3 |
| 563 | 13 | 41 | 13 | 25 | 19 | 2 | 1.5 |
| 570 | 14 | 41 | 13 | 25 | 20 | 1 | 1.6 |

EXAMPLES 6–26

Oxidation of Linear Unsaturated $C_4$-Hydrocarbons Employing Selective Catalysts In Table VI are listed additional catalysts which are within the scope of the process of the invention and which can be employed to bring about the preparation of furan via oxidation of linear unsaturated $C_4$-hydrocarbons at high hydrocarbon feed mixture concentrations employing gas flow rates and catalyst volumes so as to give nominal contact times within the limits heretofore defined. These catalysts, either supported or unsupported, were prepared by the techniques described herein. As may be seen from the table the amounts of furan produced in the off-gases by the process of the invention are >1%. In the table "BD" is 1,3-butadiene and "Bt" is 1-butene.

TABLE VI

| Ex. No. | Catalyst | % $C_4$—Hydrocarbon in Feed | Temp (°C.) | % $C_4$—Hydrocarbon Conversion | Furan Selec. (%) | % Furan in Off-gases |
|---|---|---|---|---|---|---|
| 6 | $Bi_{2.97}Fe_{0.91}Te_{0.09}Mo_2O_x$ | 24.8 BD 5.0 Bt | 493 | 17 | 27 | 1.4 |
| 7 | $Bi_3FeMo_2O_{12}/SiO_2$ | 30.1 BD | 502 | 19 | 23 | 1.3 |
| 8 | $Bi_2FeSb_3Mo_2O_x/SiO_2$ | 26.9 BD | 531 | 13 | 38 | 1.3 |
| 9 | $BiFe_{19.7}Mo_{29.5}O_x/SiO_2$ | 27.0 BD | 471 | 19 | 28 | 1.4 |
| | | | 501 | 20 | 27 | 1.4 |
| 10 | $BiCr_{0.2}Mo_{1.2}O_x/SiO_2$ | 23.8 BD 2.7 Bt | 529 | 15 | 37 | 1.5 |
| 11 | $BiCr_{39.8}Mo_{59.3}O_x/SiO_2$ | 26.5 BD | 531 | 15 | 35 | 1.4 |
| 12 | $Bi_6CrSbMo_9O_x/SiO_2$ | 26.9 BD | 501 | 15 | 36 | 1.5 |
| | | | 531 | 17 | 34 | 1.5 |
| 13 | $Bi_9Cr_8PMo_{24}O_x/SiO_2$ | 26.2 BD | 501 | 21 | 26 | 1.4 |
| 14 | $Bi_9Cr_4In_4PMo_{24}O_x/SiO_2$ | 26.2 BD | 470 | 17 | 35 | 1.6 |
| | | | 501 | 21 | 33 | 1.8 |
| | | | 531 | 22 | 32 | 1.8 |
| 15 | $Bi_9Fe_4In_4VMo_{24}O_x/SiO_2$ | 26.2 BD | 501 | 24 | 20 | 1.3 |
| 16 | $Bi_9Fe_4In_4PMo_{24}O_x/SiO_2$ | 26.2 BD | 501 | 21 | 25 | 1.4 |
| 17 | $BiIn_{10}PMo_{15}O_x/SiO_2$ | 26.1 BD | 531 | 19 | 33 | 1.6 |
| 18 | $BiInPMoO_x/SiO_2$ | 26.1 BD | 474 | 15 | 29 | 1.1 |
| | | | 507 | 21 | 31 | 1.7 |
| | | | 532 | 22 | 32 | 1.8 |
| 19 | $BiCe_{1.5}CuVPMo_{16}O_x$ | 28.2 BD | 470 | 22 | 26 | 1.6 |
| 20 | $BiCe_{11}VTeMo_{18}O_x/SiO_2$ | 26.5 BD | 503 | 21 | 25 | 1.4 |
| 21 | $BiCe_{0.67}Mo_{6.67}O_x/SiO_2$ | 26.7 BD | 472 | 20 | 27 | 1.4 |
| | | | 501 | 22 | 31 | 1.8 |
| 22 | $BiCe_{1.5}Na_{0.3}P_{0.1}Mo_{5.25}O_x/SiO_2$ | 27.7 BD | 470 | 20 | 27 | 1.5 |
| | | | 499 | 21 | 28 | 1.6 |
| 23 | $BiCe_{1.5}Na_{1.5}P_{0.5}Mo_{11.25}O_x/SiO_2$ | 27.7 BD | 501 | 21 | 28 | 1.6 |
| | | | 528 | 22 | 30 | 1.8 |
| 24 | $BiCeNa_{0.3}P_{0.1}Te_{0.1}Mo_{4.1}O_x/SiO_2$ | 26.9 BD | 502 | 21 | 30 | 1.7 |
| 25 | $BiCe_{1.5}In_{1.25}P_{1.25}Mo_{3.75}O_x/SiO_2$ | 26.9 BD | 499 | 20 | 25 | 1.3 |
| 26 | $Ca_{3.25}Bi_5As_{1.5}Mo_{8.5}O_x/SiO_2$ | 23.1 BD | | | | |

TABLE VI-continued

| Ex. No. | Catalyst | % C₄— Hydrocarbon in Feed | Temp (°C.) | % C₄— Hydrocarbon Conversion | Furan Selec. (%) | % Furan in Off-gases |
|---|---|---|---|---|---|---|
| | | 3.0 Bt | 560 | 17 | 42 | 1.9 |

EXAMPLES 27–32 (CONTROL)

Oxidation of Linear Unsaturated C₄-Hydrocarbons Employing Catalysts Known in the Art These examples, which lie outside the scope of the invention, demonstrate the optimum furan concentration in the off-gases produced with a series of catalysts prepared according to the art and tested under conditions comparable to those described in Examples 1–26. Data are listed in Table VII. Note that as the conversion of unsaturated C₄-hydrocarbons is increased while using unmodified bismuth molybdate catalysts, the furan selectivity decreases markedly. Other catalysts of the art (not containing bismuth) fail to produce furan at a level greater than 1% in the off-gases. In the table "BD" is 1,3-butadiene and "Bt" is 1-butene.

TABLE VII

| Ex. No. | Catalyst | % C₄— Hydrocarbon in Feed | Temp. (°C.) | % C₄— Hydrocarbon Conversion | Furan Select. (%) | % Furan in Off-gases |
|---|---|---|---|---|---|---|
| 27 | $Bi_2Mo_2O_9$ | 27.4 BD | 533 | 5 | 38 | 0.5 |
| 28 | $Bi_2Mo_2O_9/SiO_2$ | 24.0 BD 4.9 Bt | 465 | 10 | 30 | 0.9 |
| | | | 480 | 13 | 32 | 1.2 |
| | | | 500 | 21 | 16 | 1.0 |
| 29 | $Bi_2Mo_2O_9/SiO_2$ | 24.9 BD 4.5 Bt | 517 | 23 | 15 | 1.0 |
| 30 | $MnMoO_4$ | 27.0 BD | 471 | 15 | 10 | 0.4 |
| | | | 500 | 15 | 9 | 0.4 |
| 31 | $Fe_{5.4}PO_x$ | 27.0 BD | 473 | 19 | 10 | 0.5 |
| | | | 503 | 17 | 9 | 0.4 |
| 32 | $Co_{1.9}MoP_{1.4}O_x$ | 27.0 BD | 473 | 18 | 19 | 0.9 |
| | | | 503 | 24 | 9 | 0.6 |

We claim:

1. Catalytic vapor phase process wherein the feed stream comprising, on a molar basis, the sum of which is 100%, 10–32% of at least one linear unsaturated C₄-hydrocarbon selected from 1-butene, 2-butene and 1,3-butadiene, 10–25% oxygen, 3–30% water and 13–77% inert diluent, is contacted with a modified bismuth molybdenum oxide catalyst at 350°–600° C. at a pressure of at least 1 atmosphere (about 100 kPa) for 0.1–10 seconds, said catalyst being selected from:

(a) $BiMo_aM_bQ_cR_dO_x$ wherein M is at least one element selected from In, Ce, Cr, Fe and Cu, Q is at least one element selected from V, P, Sb and Te, R is Na or Ag, a is 0.7–60.0, b is 0.1–39.8, c is 0–7.0, d is 0–1.5 and x is such a number as is necessary to satisfy the valences of the elements, with the proviso that $a/1+b \geq 0.5$ and $a/1+b+c \geq 0.19$ and the proviso that $c > 0$ when $d > 0$; and (b) $BiMo_aAs_bZ_cO_x$ wherein Z is at least one element selected from Na and Ca, a is 1.3–2.0, b is 0.1–0.3, c is 0.3–0.7 and x is such a number as is necessary to satisfy the valences of the elements, to produce an off-gas containing at least 1% furan.

2. Process of claim 1 wherein the feed stream comprises 25–29% C₄-hydrocarbon, 14–20% oxygen, 13–20% water and 31–48% inert diluent, the temperature is 450°–550° C. and the pressure is 1–3 atmospheres (about 100–300 kPa).

3. Process of claim 2 wherein the catalyst is $BiMo_3InO_x$.

4. Process of claim 2 wherein the catalyst is $BiMo_{1.5}In_{0.5}P_{0.5}O_x$.

5. Process of claim 2 wherein the catalyst is $BiMo_{1.56}In_{0.11}P_{0.11}Ag_{0.11}O_x$.

6. Process of claim 2 wherein the catalyst is $BiMo_{6.67}Ce_{0.67}O_x$.

7. Process of claim 2 wherein the catalyst is $BiMo_{2.67}In_{0.44}Cr_{0.44}P_{0.11}O_x$.

8. Process of claim 2 wherein the catalyst is $BiMo_{1.7}As_{0.3}Ca_{0.65}O_x$.

9. Process of claim 1 wherein the catalyst is a supported catalyst.

10. Process of claim 1 wherein the catalyst is an unsupported catalyst.

11. Process of claim 1 wherein the off-gas contains at least 1.8% furan.

12. A process for producing furan comprising contacting in a feed stream comprising, on a molar basis, the sum of which is 100%, 10–32% 1,3-butadiene, 10–25% oxygen, 3–30% water and 13–77% inert diluent, in the presence of a catalyst selected from $Bi_2FeSB_3Mo_2O_x/SiO_2$ and $Bi_6CrSbMo_9O_x/SiO_2$ wherein x is such a number as is necessary to satisfy the valences of the elements, at a temperature of 350°–600° C., at a pressure of at least 1 atmosphere, for 0.1 to 10 seconds.

* * * * *